United States Patent [19]

Zeck

[11] Patent Number: 5,152,678
[45] Date of Patent: Oct. 6, 1992

[54] FLUID SAMPLING PUMP

[75] Inventor: Ted E. Zeck, Snyder, Tex.

[73] Assignee: Y-Z Industries, Inc., Snyder, Tex.

[21] Appl. No.: 799,365

[22] Filed: Nov. 27, 1991

[51] Int. Cl.$^5$ .............................................. F04B 39/10
[52] U.S. Cl. .................................... 417/401; 417/570
[58] Field of Search ............... 417/401, 559, 562, 569, 417/570

[56] References Cited

U.S. PATENT DOCUMENTS

| | | | |
|---|---|---|---|
| 2,122,020 | 6/1938 | Barks | 417/489 X |
| 3,312,178 | 4/1967 | Rotter et al. | 417/254 |
| 3,995,966 | 12/1976 | Blancha | 417/559 X |
| 4,137,017 | 1/1979 | Lonardo | 417/559 X |
| 4,452,573 | 6/1984 | Samuel | 417/401 |
| 4,470,775 | 9/1984 | Lonardo | 417/569 |
| 4,531,895 | 7/1985 | Zeck | 417/401 |
| 4,645,431 | 2/1987 | Spencer | 417/401 |

Primary Examiner—Leonard E. Smith
Attorney, Agent, or Firm—Wendell Coffee

[57] ABSTRACT

A pump for sampling fluids from a pipe line has a very high volumetric efficiency. The pump has a plunger that substantially completely displaces the volume of the cavity within which it works. To prevent flow of the fluid from the pipe line to the sampling container when the pipe line pressure is higher than the sampling container, a floating plunger liner has a passage open to the pipe line pressure. The pipe line pressure will force the liner against the outlet valve if the pipe line pressure is higher than the collecting vessel pressure. When the plunger evacuates the cavity the pressure in the cavity will be greater than the pipe line pressure and the outlet pressure and will force the plunger liner downward to open the outlet valve to permit flow of the fluid from the cavity through the outlet to the collecting vessel. If the pressure is lower in the cavity than either the pipe line or the collecting vessel, there will be no flow from the collecting vessel but only flow from the pipe line.

7 Claims, 1 Drawing Sheet

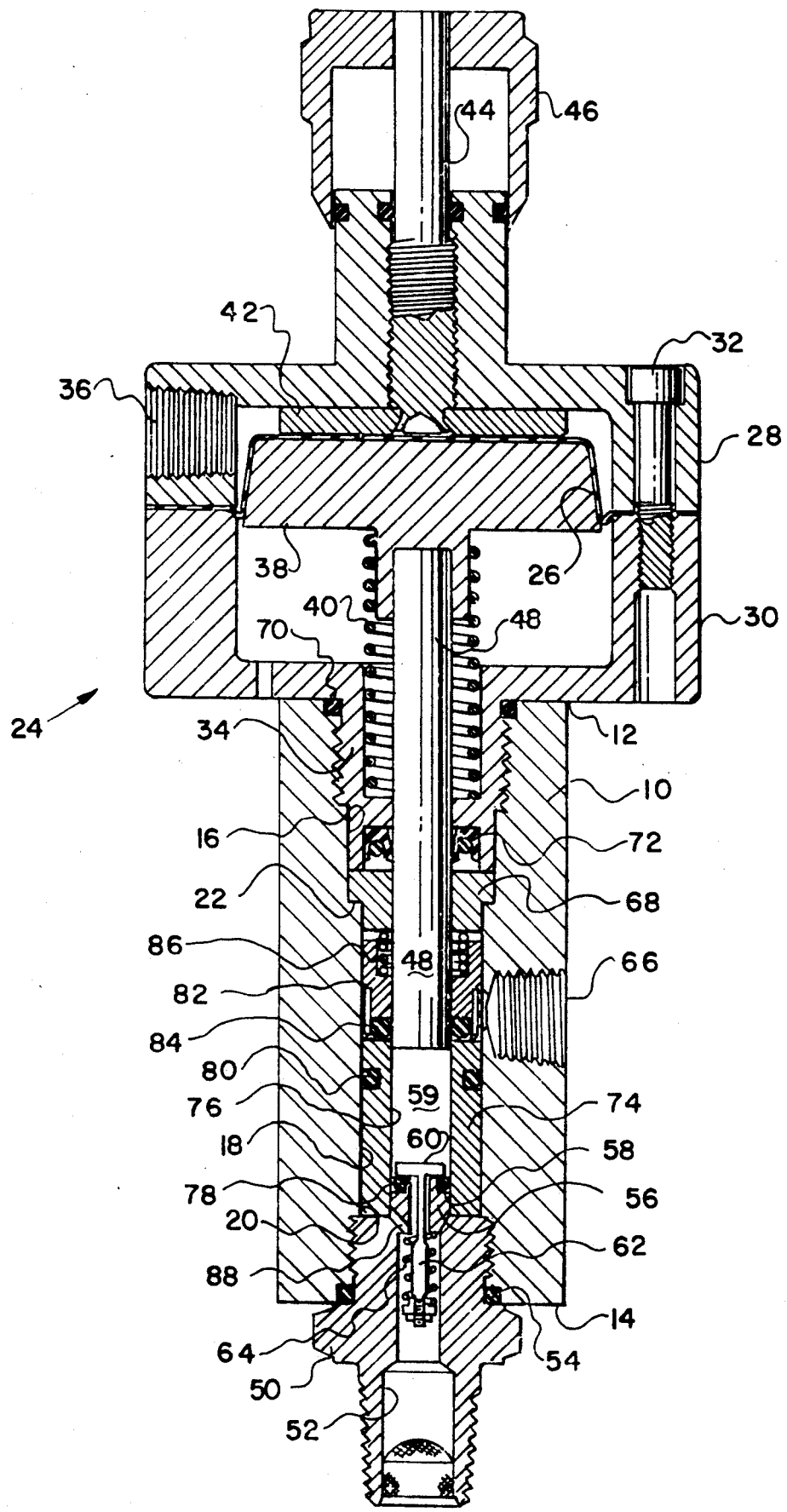

FLUID SAMPLING PUMP

BACKGROUND OF THE INVENTION

(1) Field of the Invention

This invention relates to sampling fluids and particularly for a 99+% volumetric efficient pump for sampling fluids and especially gases as well as liquids from pipe lines. Persons concerned with the quality of fluids being transmitted in pipe lines have ordinary skill in this art.

(2) Description of the Related Art

The inventor previously received U.S. Pat. No. 4,531,895 on the Jul. 30, 1985 for a Gas Sampling Pump. That patent disclosed a pump having a very high volumetric efficiency in taking samples from a pipe line. That pump included an exterior line to the pump so there would be a balanced valve within the pump. Also, that pump had at least three O-rings sealing the riciprocating plunger from the bore within which it worked.

Use of this pump has indicated certain limitations of its utility because of the friction between the O-rings and the plunger. Also, the exterior line identified by the numeral 84 in the patent as the balance conduit, made it clumsy or difficult to install and remove for service.

SUMMARY OF THE INVENTION

(1) Progressive Contribution to the Art

This invention discloses a fluid pump which is suitable for pumping liquids as well as gases wherein the plunger slides through only two seals, one of which is a low friction seal and the other of which is an O-ring. Also, an internal balancing vent is provided. Balancing results from a floating plunger liner having the capability to float up and down for different cycles of the pump.

(2) Objects of this Invention

An object of this invention is to take samples of fluid flowing in a pipeline.

Another object of this invention is to periodically take the same volume of fluid sample.

Another object of this invention is to achieve the above with a device having the ability to easily and accurately adjust the volume of the samples.

A further object is to accomplish the above with a pump having a balanced outlet valve to permit it to sample from a pipeline where the pressure is less than or greater than the pressure at the outlet of the pump without manual adjustments or attention.

Further objects are to achieve the above with devices that are sturdy, compact, durable, lightweight, simple, safe, efficient, versatile, ecologically compatible, energy conserving, and reliable, yet inexpensive and easy to manufacture, install, operate, and maintain.

Other objects are to achieve the above with a method that is rapid, versatile, ecologically compatible, energy conserving, efficient, and inexpensive, and does not require highly skilled people to install, operate, and maintain.

The specific nature of the invention, as well as other objects, uses, and advantages thereof, will clearly appear from the following description and from the accompanying drawings, the different views of which are not necessarily scale drawings.

BRIEF DESCRIPTION OF THE DRAWINGS

The drawing is an axial sectional view of a sampler pump according to this invention.

As an aid to correlating the terms of the claims to the exemplary drawing(s), the following catalog of elements and steps is provided:

10—housing
12—power end
14—housing outlet end
16—housing bore
18—C.W.S.
20—inlet end C.W.S.
22—outlet end C.W.S.
24—motor
26—diaphram
28—upper case
30—lower case
32—bolts
34—neck
36—motor inlet
38—piston
40—motor spring
42—motor stop
44—piston stop screw
46—nut
48—plunger
50—inlet check body
52—stepped bore
54—O-ring
56—inlet pedestal
58—valve seat
59—cavity
60—disc valve
62—valve stem
64—spring
66—outlet
68—annular stop
70—O-ring
72—low friction seal
74—plunger liner
76—liner bore
78—O-ring
80—liner seal passage
82—outlet valve
84—outlet seat
86—spring
passage

DESCRIPTION OF THE PREFERRED EMBODIMENTS

Referring to the drawing there may be seen a fluid sampling pump. Pump housing 10 has a power end 12 and an inlet end 14. Housing bore 16 extends through the housing. The housing bore will have a cylindrical working section 18 at the inlet end 14. The cyclindrical working section itself will have an inlet end 20 and an outlet end 22.

Motor 24 is connected to the housing 10 at the outlet end. The motor includes diaphragm 26 which is tightly clamped between upper motor case 28 and lower motor case 30. The upper and lower cases are clamped together by a plurality of bolts 32 (only one showing in the drawing). The lower case has a threaded neck 34 which threads into the power end of the housing bore 16. It will be noted that where the neck 34 threads into the housing bore, that the housing bore is enlarged and is greater diameter than the cylindrical working section 18 of the housing bore. The upper case has motor inlet 36 which is, on the pressure side of the diaphragm 26. A source of pneumatic operating gas is connected to the inlet 36 which therefore forms means for supplying pneumatic pressure such as pressurized air or pressurized gas to the diaphragm with pulses at predetermined intervals. This is explained in detail in the previous U.S. Pat. No. 4,531,895 identified above.

The diaphragm 26 fits over guide or piston 38. Helical compression motor spring 40 pushes the diaphragm guide 38 and thus the diaphragm 26 upward. The spring extends from the lower case 30 to the bottom of the piston 38. The upward travel of the diaphragm and guide is limited by motor stop 42. The position of the motor stop 42 is controlled by micrometer screw 44 to which it is attached. The micrometer screw is attached to micrometer nut 46. An O-ring between the screw 44 and the upper case 28 prohibits the loss of the motor gas entering through the motor inlet 36. The O-ring between the upper case and the micrometer nut provides friction so that once the nut has been set upon a desired volume it will not be easily accidently moved from that setting.

Plunger 48 is a cylindrical rod extending from the diaphragm piston 38 into the cylindrical working section 18 of the housing bore 16. It is preferred the plunger be made of a wear resistant material such as polished stainless steel or ceramic.

Inlet plug or check body 50 is threaded into the inlet end 14 of the housing bore 16. Again, it will be noted that the bore at the point where the inlet check body is threaded is larger than the cylindrical working section 18. The plug has stepped bore 52 therethrough. The exterior of the inlet check body is sealed by O-ring 54 to the housing 10.

An annular inlet pedestal 56 of inlet plug 50 extends into the cylindrical working section 18 of the housing bore. Circular inlet valve seat 58 on the inlet pedestal is co-axial with the cylindrical working section 18 bore. Flat circular disc valve 60 is co-axial with the valve seat 58 and seated upon the valve seat 58.

Valve stem 62 extends from the disc valve 60 into the stepped bore 52. Helical compression spring 64 extends from a step within the bore 52 to a nut on the bottom of the stem 62. Therefore it may be seen that the spring biases the disc valve against the seat into a closed position.

The plunger 48 will rest upon the valve 60 and terminate the downward stroke of the diaphragm 26. Therefore it may be seen by a setting of the motor stop 42 by the micrometer nut 46 will accurately determine the stroke of the plunger. Inasmuch as the plunger works with a snug sliding fit within a bore, that a precise amount of fluid will be displaced with each stroke of the diaphragm 26.

Outlet 66 extends through the housing from the housing bore 16 to the exterior of the housing. It is threaded to receive a conduit to a receiver well known but not shown in the drawings.

Those with ordinary skill in the art will understand that the structure described to this point is basically old and it is described in the prior U.S. Pat. No. 4,531,895 except specifically for the micrometer nut upon the screw 44, and the material of the plunger 48.

Annular stop 68 is within the bore 16. A flange of stop 68 fits within the bore 16 at the outlet end 22 of the cylindrical working section 18. A portion of the annular stop 68 extends on within the cylindrical working section 18. The bore through the stop 68 is co-axial with the cylindrical working section. The stopp is fixed in the housing 10 by threaded neck 34 and sealed by the contact of the flange upon a shoulder and also by O-ring 70.

Between the stop 68 and the neck 34 is low friction seal 72 which has the effect of sealing the plunger 48 to the housing 10. As may be seen in the drawing, the seal 72 is fitted within a recess in the neck 34 and extends between the neck 34 and the stop 68. However, since the stop 68 and this portion of the neck 34 are also sealed to the housing, this seal itself in effect seals the plunger to the housing. As stated before it is a low friction seal. Annular plunger liner 74 is telescoped within the working section 18 of the housing bore 16. The exterior surface of the liner 74 is cylindrical and forms a snug sliding fit with the working bore 18. The plunger liner has bore 76 therethrough which has an inlet end adjacent to the inlet end 20 of the cylindrical working section. The bore 76 is fluidly sealed around the inlet pedestal 56 by O-ring 78. As may be seen, the O-ring 78 works with the valve seat 58 of the pedestal 56. Liner seal 80 in the form of an O-ring seals the exterior surface of the plunger liner 74 to the cylindrical working section 18 of the housing bore 16.

The outlet 66 is between the annular stop 68 and the liner seal 80. Therefore the only path for fluid within the cavity 59 within the plunger liner 74 between the plunger 48 and the disc valve 60 is at the outlet 66. I.e., there is no gas passageway when the disc valve 70 is seated upon its valve seat 58 with the O-ring 78 except between the liner seal 80 and the stop 68. The passage of gas from the cavity is normally blocked by annular outlet valve 82. The annular valve 82 is telescoped within the cylindrical working section 18 between the plunger liner 74 and the stop 68. The face of the outlet valve 82 adjacent to the liner 74 is normally sealed by O-ring 84 which forms a valve seat between the valve 82 and the liner 74. The annular valve 82 is biased downward by helical compression spring 86 between the stop 68 and the outlet valve 82. The O-ring 84 of the outlet seat also forms a seal between the plunger 48 and the valve 82.

The outlet valve is balanced by vent or passage 88 extending through the inlet check body 50. Specifically the passage 88 extends from within the bore 52 to the cylindrical working section 18 of the housing bore 16. This is an area between the O-ring seal 54 of the check body 50 to the housing 10 and the liner seal 80 sealing the liner to the housing 10. Therefore between the liner and the inlet plug there will be the inlet pressure of the gas which is the pressure in the pipeline which is being sampled.

If the pressure within the cavity 59 is less than the pressure within the pipeline as it will be normally when the plunger is on the up stroke, the disc valve 60 will be off the seat and also the pressure on the inlet end of the plunger liner 56 will permit the inlet liner to move upward against the outlet seat 84. If the pressure within the cavity 59 is approximately the same as the pipeline pressure in the inlet check body bore 52 the spring 58 will close the disc valve 60 and the spring 86 will push the outlet valve 82 downward and also push the plunger liner 74 downward. This will be the condition while the plunger is in the raised position. It will be understood that the plunger may be in the raised position an extended length of time between pressure pulses which cause the plunger 48 to reciprocate. When the plunger 48 starts downward into the cavity 59 the increased pressure will cause the valve 82 to move away from the plunger liner 74 permitting the fluid within the cavity 59 to flow outward through the outlet 66.

It will be understood that the parts specifically, the plunger liner, the plunger, and the annular valve, all form snug, slidable fits. There is ample passageway between these parts except where they are sealed by O-ring seals, or the low friction seals 72 for the fluid to pass between them. However, they form snug, slidable fits so that when the plunger 48 pushes against the valve 60, there is substantially no volume above or around the edges of the disc valve 60 to the plunger 48. Therefore, this is the condition that results in a very high volumetric efficiency. As soon as the plunger 48 pulls away from the disc 60, the reduced pressure within the cavity 59 will cause the disc 60 to open and also this reduced pressure will permit the spring 86 to close the outlet valve 82 against the O-ring valve seat 84. Therefore, a very high percentage of the fluid within the cavity 59 will be expelled through the outlet 66 each and every stroke. If the pressure in the pipe line is greater than the pressure of outlet 66, the plunger will be forced upward by the imbalance of pressure applied by the fluid pressure through passage 88 and impinging upon the lower area of plunger liner 74. This action forces outlet valve 82 to close spring 86 and be stopped by the annular stop 68. This action forces the O-ring 84 to seal upon the seal end of the plunger liner and plunger 48, thereby not permitting the fluid to flow out the outlet 66. When the plunger is stroked to displace the volume of gas(fluid) in chamber 59 to a pressure greater than the impinging pressure on the lower end of plunger liner 74 the increase in pressure bears against the seal end of plunger liner 74 and forces the outlet seat to separate from the seat on the plunger liner 74 and permits the fluid in chamber 50 to be expelled out past the outlet seat O-ring 84. When the plunger action stops the pipeline pressure again forces the plunger liner 74 to close the outlet O-ring 84, to seat and stop the flow of fluid out outlet 66.

The embodiment shown and described above is only exemplary. I do not claim to have invented all the parts, elements or steps described. Various modifications can be made in the construction, material, arrangement, and operation, and still be within the scope of my invention.

The restrictive description and drawings of the specific examples above do not point out what an infringement of this patent would be, but are to enable one skilled in the art to make and use the invention. The limits of the invention and the bounds of the patent protection are measured by and defined in the following claims.

I claim as my invention:

1. The process of operating a fluid sampling pump, which pump includes
   a. a pump housing having a power end and an inlet end,
   b. a housing bore extending through the housing having
   c. a cylindrical working section having an inlet end and outlet end,
   d. a cylindrical plunger co-axial with the cylindrical working section extending from the power end of the housing to within the cylindrical working section of the housing bore,
   e. power means for reciprocating the plunger interconnecting the housing power end and the plunger,
   f. an annular inlet pedestal having a bore and its exterior sealed to the inlet end of the housing and extending into the inlet end of the cylindrical working section of the housing bore,
   g. a circular inlet valve seat on the inlet pedestal co-axial with the working section bore,
   h. a flat circular disc valve co-axial with and upon the valve seat,
   j. an outlet to a receiver through the housing from the housing bore;
   k. wherein the improved method comprises the steps of
   l. providing a floating plunger liner having a snug sliding fit with the housing bore, said plunger lining having an inlet end and an otlet end.
   m. Venting pressure from the inlet pedestal bore to the inlet end of the plunger liner, thereby
   n. forcing the plunger liner upward against a floating outlet valve at the outlet end of the floating plunger liner, if the pressure within the inlet pedestal bore is greater than the pressure at the outlet to the receiver, and
   o. forcing the floating valve and the floating plunger liner downward if the pressure at the outlet to the receiver is greater than the pressure in the inlet pedestal bore.

2. A fluid sampling pump including
   a. a pump housing having a power end and an inlet end,
   b. a housing bore extending through the housing having
   c. a cylindrical working section having an inlet end and outlet end,
   d. a cylindrical plunger co-axial with the cylindrical working section extending from the power end of the housing to within the cylindrical working section of the housing bore,
   e. power means for reciprocating the plunger interconnecting the housing power end and the plunger,
   f. an annular inlet pedestal having a bore and its exterior sealed to the inlet end of the housing and extending into the inlet end of the cylindrical working section of the housing bore,
   g. a circular inlet valve seat on the inlet pedestal co-axial with the working section bore,
   h. a flat circular disc valve co-axial with and upon the valve seat,
   j. an outlet to a receiver through the housing from the housing bore;
   k. wherein the improvement comprises in combination with the above:
   l. an annular stop fixed to the housing co-axially with and at the outlet end of the cylindrical working section of the housing bore,
   m. an annular housing seal between the stop and the power means sealing the plunger to the housing,
   n. an annular plunger liner telescoped in the cylindrical working section of the housing bore,
   o. said plunger liner having
      i. a snug sliding fit with the housing bore,
      ii. an inlet end bore fluidly sealed around said inlet pedestal, and
      iii. a liner seal between its exterior surface and the working section of the housing bore,
   p. said outlet to a receiver between said annular stop and said liner seal, q. an annular outlet valve telescoped in the cylindrical working section of the housing bore between said plunger liner and said stop,
r. an outlet valve seat between the outlet valve and plunger liner,
s. said outlet valve seat forming a seal between the outlet valve and plunger liner and also a seal between the outlet valve and the plunger, and
t. a compression spring between said stop and said outlet valve.

3. The invention as defined in claim 2 further comprising:
u. a valve stem on said inlet valve,
v. extending into the pedestal bore,
w. an inlet spring between the inlet valve seat and the stem.

4. The invention as defined in claim 2 wherein said motor means includes:
u. a diaphragm.
v. means for supplying the diaphragm with a pulse of pneumatic pressure at predetermined intervals thereto,
w. said diaphragm connected to said plunger so as to force the plunger against the inlet valve,
x. a power stop to limit the upward movement of said diaphragm,
y. said power stop connected to a screw having a micrometer nut thereon.

5. The invention as defined in claim 2 further comprising a vent between said pedestal bore and the inlet of said plunger liner.

6. The invention as defined in claim 5 wherein said plunger forms a snug sliding fit within the bore of said plunger liner.

7. The invention as defined in claim 5 wherein the above structure functions to permit the valve to obtain samples from the pipe line regardless of the pressure within the pipe line in relationship to the pressure at the outlet to a receiver.

* * * * *